United States Patent [19]

Habermann et al.

[11] Patent Number: 5,106,479
[45] Date of Patent: Apr. 21, 1992

[54] METAL/METAL OXIDE ELECTRODE FOR DETERMING CHLORINE

[75] Inventors: Wolfgang Habermann, Mainz; Axel Anderlohr, Mannheim; Wolfgang Steiner, Friedelsheim, all of Fed. Rep. of Germany

[73] Assignee: BASF Aktiengesellschaft, Ludwigshafen, Fed. Rep. of Germany

[21] Appl. No.: 571,284

[22] Filed: Aug. 23, 1990

[30] Foreign Application Priority Data

Sep. 14, 1989 [DE] Fed. Rep. of Germany ....... 3930671

[51] Int. Cl.$^5$ .............................................. G01N 27/26
[52] U.S. Cl. ................................. 204/416; 204/400; 204/192.22; 204/192.13; 204/290 F
[58] Field of Search .................. 204/400, 416, 192.13, 204/290 F, 192.22

[56] References Cited

U.S. PATENT DOCUMENTS

| 3,956,094 | 5/1976 | Capuano | 204/195 R |
| 4,581,117 | 4/1986 | Asano et al. | 204/290 F |
| 4,589,969 | 5/1986 | Yurkov et al. | 204/290 F |
| 4,849,081 | 7/1989 | Ross | 204/192.22 |

FOREIGN PATENT DOCUMENTS 1101807  1/1968  United Kingdom.

Primary Examiner—John Niebling
Assistant Examiner—Bruce F. Bell
Attorney, Agent, or Firm—Keil & Weinkauf

[57] ABSTRACT

A metal/metal oxide electrode for determining chlorine in aqueous solutions comprises a metallic tantalum core on which there is non-porous tantalum suboxide.

5 Claims, No Drawings

METAL/METAL OXIDE ELECTRODE FOR DETERMING CHLORINE

The present invention relates to a metal/metal electrode for the potentiometric and amperometric determination of chlorine in acidic aqueous solutions.

Chlorine in aqueous solutions has hitherto been measured by using noble metal redox electrodes. It has emerged that redox electrodes made of these metals are, because of their good electron exchange conditions, not selective and not suitable for quantitative determination of chlorine. Mixed potentials are set up on these electrode materials in the presence of chlorine and oxygen, while there is some catalytic reaction of chlorine when hydrogen is also present.

The electrode materials made of tungsten and molybdenum which are mentioned in British Patent 1,101,807 and are employed particularly for measuring chlorine in gases are indeed substantially selective for chlorine but display deficiencies in reproducibility and zero point stability.

Chemical analytical methods such as iodometry are not always suitable for continuous analysis and are unsuitable for measuring chlorine concentrations $\leq 5$ ppm.

It is an object of the present invention to measure chlorine selectively and continuously in acidic aqueous solutions, especially in the concentration range $\leq 1$ ppm, in the presence of hydrogen, oxygen, hydrogen peroxide or other substances which have hitherto interfered with analysis.

We have found that this object is achieved by using for the potentiometric and amperometric determination of chlorine in acidic aqueous solutions a metal/metal oxide electrode which is composed of a metallic tantalum core whose surface is coated with a non-porous layer of tantalum suboxide.

The tantalum suboxide has the formula $Ta_2O_{5-X}$. The average value of X in the outer suboxide layer, which can be from 15 to 60 Å thick, ought to be from 0.03 to 0.06. The values for X in the suboxide layer adjacent to the metal can be from 0.1 to 2 in order to ensure sufficient conductivity. The conductivity in the suboxide layer adjacent to the metal can be a $\geq 1.2 \times 10^1 \Omega^{-1} \times cm^{-1}$, while that in the outer suboxide layer, which is crucial for the catalytic reaction, ought to be from $10^{-8}$ to $10^{-4} \Omega^{-1} \times cm^{-1}$.

The total thickness of the tantalum suboxide layer must be from 60 to 150 Å in order to have sufficient selectivity for chlorine and chemical resistance to the electrolyte. The preferred total thickness of the suboxide layer is from 80 to 120 Å.

The starting material used for the metal/metal oxide electrode is tantalum which complies with ASTM and has a purity of $\geq 99.8\%$ by weight and contains $\leq 0.04\%$ niobium, $\leq 0.01\%$ carbon, $\leq 0.01\%$ iron, $\leq 0.01\%$ titanium, $\leq 0.03\%$ tungsten, $\leq 0.005\%$ silicon, $\leq 0.01\%$ nickel, $\leq 0.01\%$ molybdenum, $\leq 0.03\%$ oxygen, $\leq 0.01\%$ nitrogen and $\leq 0.001\%$ hydrogen.

The tantalum is employed in the form of rods, plates, wires or wool for the fabrication of the metal/metal oxide electrode, and the material ought to have a smooth and non-porous surface.

To produce the suboxide layer, the tantalum surface is initially cleaned with a chlorohydrocarbon solvent, e.g. trichloromethane, to remove organic impurities, and the residual solvent is then removed with a polar non-chlorohydrocarbon solvent, e.g. acetone or isopropanol. The oxide on the surface of the tantalum is removed by back sputtering in a noble gas atmosphere free of oxygen at from $5 \times 10^{-3}$ to $5 \times 10^{-2}$ mbar. Suitable and preferred noble gases are argon and neon because the best surface cleaning is obtained with these gases. The back sputtering is carried out with a DC voltage of from 1 to 3 KV, preferably 2 KV, the tantalum surface forming the cathode (negative).

The oxide-free tantalum surface is then oxidized in air or oxygen at from $-20°$ C. to $+200°$ C.

The tantalum surface is preferably oxidized first with air which is free of carbon dioxide and low in water vapor at from $+20°$ to $+50°$ C. and under a pressure of 1 bar for about 6 to 24 h. The surface layer is then stabilized in the presence of oxygen under a pressure of from 0.3 to 1.5 bar and at from 20 to 50° C for about 5 to 30 h. The final treatment of the suboxide layer is carried out in aqueous alkali metal chloride or hydrochloric acid solution in the presence of chlorine.

This treatment is preferably carried out in aqueous 2 to 5 % by weight alkali metal chloride solution or hydrochloric acid which contains from 500 to 3000 ppm free chlorine at from $+15°$ to $+40°$ C.

The redox electrode produced in this way is suitable for the amperometric or potentiometric determination of chlorine in aqueous electrolytes. The potentiometric measurement is preferably carried out by using the metal/metal oxide electrode as the cathode with an auxiliary electrode made of platinum or a platinum metal at a current density of from 0.1 to 3 $\mu A/cm^2$ of surface area. The resting potential of the metal/metal oxide cathode in the absence of chlorine ought to be about 10 mV relative to the pH-dependent hydrogen deposition potential in the medium.

The reference electrodes used for determining the potential, which is a measure of the chlorine content, are calomel, silver/silver chloride or Thalamid electrodes.

The amperometric measurement, e.g. with the aid of a galvanic cell, is preferably carried out using tantalum wool coated with tantalum suboxide as cathode for the chlorine reduction, while a suitable anode is a silver sponge or a hydrogen electrode with adequate hydrogen storage capacity. Hydrogen electrodes which can be used are Raney nickel anodes gassed with hydrogen or dehydrogenating an alkanol.

The methods according to the invention are particularly suitable for measuring chlorine and traces thereof in process and waste water, in purifying drinking water and for measuring the chlorine content in swimming baths.

EXAMPLE 1

A wire composed of 99.8% by weight tantalum, containing $\leq 0.04\%$ niobium, $\leq 0.01\%$ iron, $\leq 0.01\%$ nickel and $\leq 0.01\%$ molybdenum and having a diameter of 2 mm and a length of 150 mm is rinsed with trichloromethane to remove organic impurities and then with isopropanol. Drying and degassing of the surface at $+80°$ C. under 30 mbar for 30 minutes are followed by removal of the oxide on the surface of the tantalum wire by back sputtering. For this, the tantalum wire forms the cathode and is cleaned under an oxygen-free argon atmosphere at $1 \times 10^{-2}$ mbar with a DC voltage of 2 KV. The tantalum wire is then treated under 1 bar of air which is free of water vapor and carbon dioxide at $+30°$ C. for about 8 h. The tantalum wire is then exposed to 1 bar of oxygen at $+25°$ C. for 8 h. After this treatment, 25 mm at one end of the tantalum wire is immersed in 2.5% by weight aqueous hydrochloric acid which contains ~1,000 ppm chlorine for about 3 h. The tantalum wire is then sheathed in Teflon reinforced with glass fiber, leaving 10 mm at each end of the wire uncovered. The end treated with chlorine-containing hydrochloric acid is used as measuring electrode, while the other end is used for the connection. The oxide on the surface of this end is removed mechanically, and it is then rhodanized. Analysis of the suboxide layer on the measuring electrode shows that the outer suboxide layer is about 50 Å thick and has the formula $Ta_2O_{5-x}$ where X is 0.04. The total thickness of the suboxide layer is about 85 Å. To measure the chlorine in waste water containing hydrochloric acid, the measuring electrode is used as cathode with a platinum auxiliary electrode and a current of ~2 μA. A 6 V DC voltage source with a series resistance of 6 mΩ is used for polarization. The potential of the redox electrode is measured against a silver/silver chloride reference electrode at high resistance. The potentials, converted to the standard hydrogen electrode, measured in a 2% by weight aqueous sodium chloride solution containing hydrochloric acid for different chlorine concentrations were as follows:

| $Cl_2$ concentration ppm | Potential $E_h$ mV |
|---|---|
| 0 | +10 |
| 0.01 | +45 |
| 0.1 | +75 |
| 1.0 | +307 |
| 10 | +720 |
| 100 | +1,076 |

This electrode was used continuously for determining chlorine in waste water containing hydrochloric acid for 6 months without any changes in the accuracy of measurement occurring.

EXAMPLE 2

For amperometric measurement, 50 ml of tantalum wool made of wire 0.2 mm thick and weighing 65 g are cleaned, oxide residues are removed and reoxidation in air and oxygen is carried out, as in Example 1. All the tantalum wool is then treated in aqueous 5% by weight hydrochloric acid which contains 200 ppm chlorine for about 3 h. After this treatment, the tantalum wool is packed into a glass tube of diameter 20 mm and length 180 mm and connected to a rhodinized tantalum wire which is 2 mm thick. In the center of the wall of the glass tube there is an opening which is 10 mm wide, is covered by a cation exchanger membrane and separates the counter electrode, a silver sponge electrode, from the tantalum electrode. The silver sponge electrode is immersed in a 5% by weight aqueous solution of sodium chloride. To measure the chlorine content in a medium it is passed through the tube containing the oxidized tantalum wool. The reactions taking place are reduction of chlorine at the tantalum cathode $$Cl_2 + 2e \rightarrow 2Cl^-$$

and oxidation of silver at the silver sponge anode $$2Ag + 2Cl^- \rightarrow 2AgCl + 2e.$$

The chlorine content is determined by measuring the current from the reaction at low resistance. The current from the reaction with a throughput of 1,000 ml/h waste water is ~0.7 mA/ppm chlorine. At constant throughput, the current from the reaction is proportional to the chlorine concentration.

We claim:
1. A metal/metal oxide electrode for the potentiometric and amperometric determination of chlorine in acidic aqueous electrolytes which consists essentially of a metallic tantalum core whose surface is coated with a non-porous layer of tantalum suboxide.
2. A metal/metal oxide electrode as claimed in claim 1, in which the tantalum suboxide has the formula $Ta_2O_{5-x}$.
3. A metal/metal oxide electrode as claimed in claim 2, wherein the non-porous layer contains an inner suboxide layer and an outer suboxide layer and in which the average value of X in the outer suboxide layer is from 0.03 to 0.06 and the conductivity of the said layer is from $10^{-8}$ to $10^{-4} \Omega^{-1} cm^{-1}$.
4. A metal/metal oxide electrode as claimed in claim 1, in which the total thickness of the tantalum suboxide layer is from 80 to 120 Å.
5. A metal/metal oxide electrode as claimed in claim 1, in which the tantalum suboxide is generated on the metallic tantalum core by back sputtering under from $5 \times 10^{-3}$ to $5 \times 10^{-2}$ mbar of noble gases, subsequent oxidation of the tantalum surface with oxygen at from $-20°$ C. to $+200°$ C., and subsequent treatment of the surface in aqueous hydrochloric acid containing chlorine.

* * * * *